(12) United States Patent
Ek

(10) Patent No.: US 6,209,544 B1
(45) Date of Patent: *Apr. 3, 2001

(54) TURNING RESTRAINING DEVICE

(76) Inventor: Robert Ek, Odlingsvägen 46, Alvesta (SE), 342 33

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,639

(22) PCT Filed: Nov. 28, 1997

(86) PCT No.: PCT/SE97/02001

§ 371 Date: May 28, 1999

§ 102(e) Date: May 28, 1999

(87) PCT Pub. No.: WO98/23188

PCT Pub. Date: Jun. 4, 1998

(51) Int. Cl.[7] .................................................. A61B 19/00
(52) U.S. Cl. ............................................. 128/869; 128/875
(58) Field of Search ........................... 128/846, 869–876; 5/630, 636, 637, 638

(56) References Cited

U.S. PATENT DOCUMENTS

| 2,044,390 | * | 6/1936 | Kiehs | 128/874 |
| 2,693,177 | * | 11/1954 | Barstow | 128/874 |
| 2,827,898 | * | 3/1958 | Thompson | 128/874 |
| 3,265,065 | | 8/1966 | Jillson | 128/134 |
| 3,566,864 | * | 3/1971 | Garrow | 128/874 |
| 3,788,309 | * | 1/1974 | Zeilman | 128/874 |
| 4,742,821 | * | 5/1988 | Wootan | 128/873 |
| 4,832,053 | * | 5/1989 | McCarthy | 128/874 |

FOREIGN PATENT DOCUMENTS 1153370   5/1969   (GB) .

* cited by examiner

Primary Examiner—Michael A. Brown
(74) Attorney, Agent, or Firm—Jacobson, Price, Holman & Stern, PLLC

(57) ABSTRACT

A restraining device includes an article of dress (3) or a harness, which is put on or fastened around at least one part of the body. Two parts (4, 5) of a strap of about the same length extend from the backside of the article of dress (3) or the harness and outwards to the two sides (9) of the bed. In order to prevent a person being in bed from turning his body in one of the other directions from a position lying on the stomach to a position lying on the back, said strap parts (4, 5) are attached along the entire backside of the article of dress (3) or harness or are attached to the sides (6) of the article of dress (3) or harness. The free ends (7, 8) of the strap parts (4, 5) are extended from the sides of the article of dress/harness to the closest side (9) of the bed (1) and are attachable to this side (9), whereat the length of the two strap parts (4, 5) can be adjusted by means of a buckle (11) or the like so that the strap parts (4, 5) are completely straightened when the person has turned his body not more than about 90°.

12 Claims, 3 Drawing Sheets

TURNING RESTRAINING DEVICE

The invention concerns a device for preventing a person being in bed from turning his body in one or the other direction from a position lying on the stomach to a position lying on the back, said device including an article of dress or a harness, which is put on or fastened around at least one part of the body, whereat two parts of a strap of about the same length extend from the back side of the article of dress or the harness and ourwards to the two sides of the bed. Persons who are disposed for snoring can be prevented from snoring if they are sleeping on the stomach or on one of the two sides. To sleep on the back might be dangerous. The device according to the invention will prevent a person from turning his body in one or the other direction from a position lying on the stomach to a position lying the back. However, the person can easily turn his body about 90° from a position on the stomach.

Two embodiments of the invention will be described and are shown in the accompanying drawings.

Figure 1:
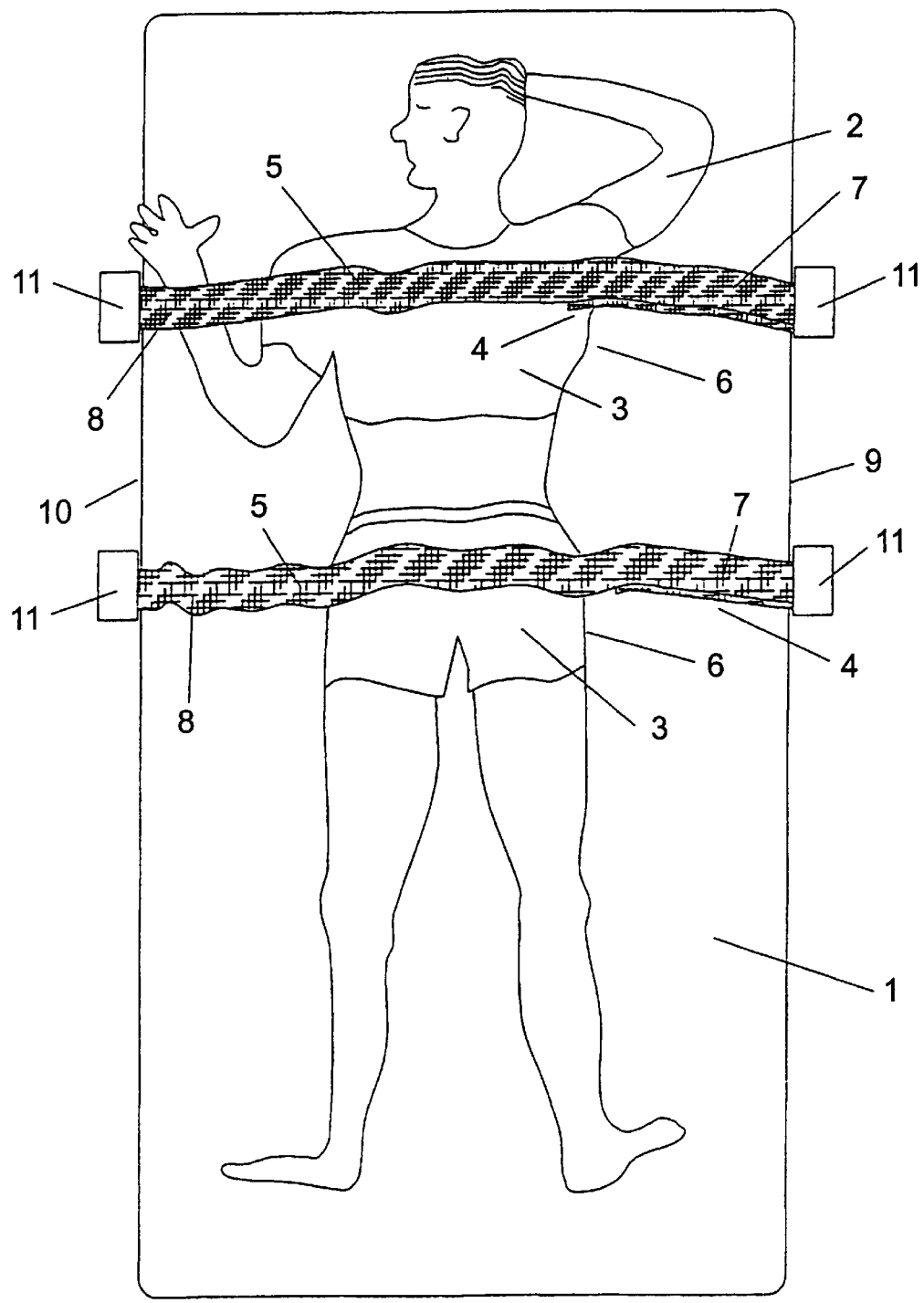
FIG. 1 is a plan view of a person with the device according to a first embodiment of the invention.
Figure 2:
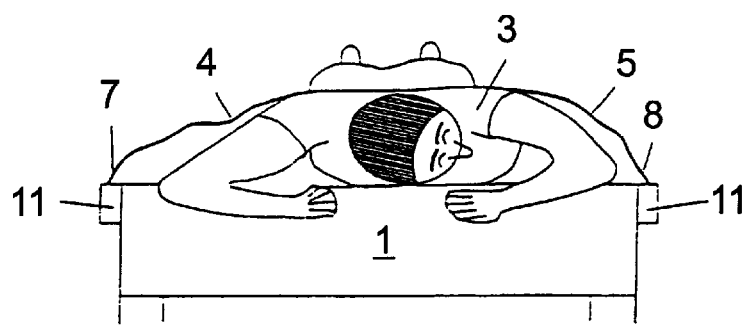
FIG. 2 is a front view of FIG. 1.
Figure 3:
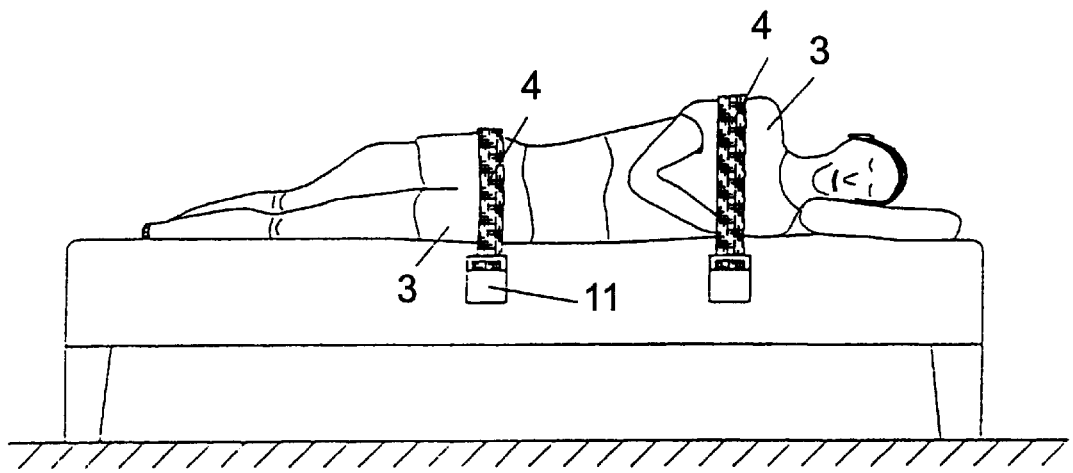
FIG. 3 is a side view of the device according to the invention.
Figure 4:
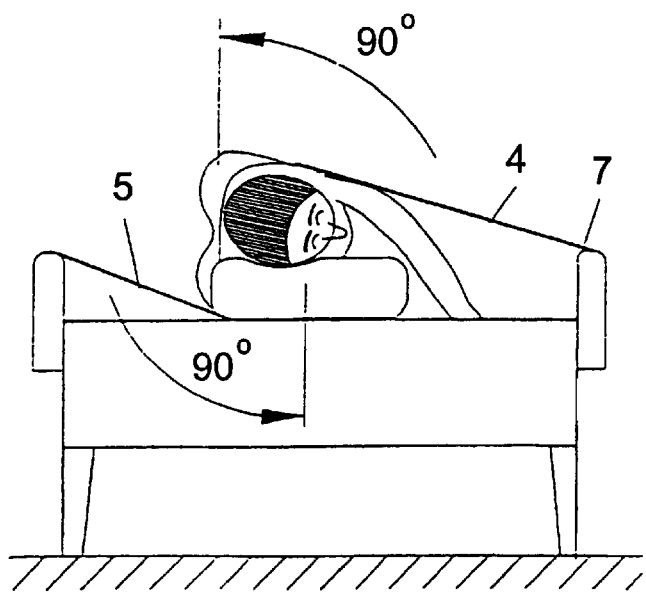
FIG. 4 is a front view of FIG. 3.

FIGS. 1 and 2 shows a bed 1 in which a person 2 is lying. One device according to the invention is put on the upper body and a second device according to the invention is put on the lower part of the body. The device includes an article of a dress 3. Two strap parts 4, 5 are attached along the entire back side of the article of dress 3. The strap parts can alternatively be attached only at each side 6 of the article of dress instead of along the entire back side. The free ends 7, 8 of the strap parts are extended from the sides of the article of dress to the closest side 9, 10 of the bed and are attachable to these sides. The length of the two strap parts 4, 5 can be adjusted by means of a buckle 11 or the like so that the strap parts are compeltely straightened when the person has turned his body not more than about 90°, see FIGS. 3 and 4.

The shown buckles 11 are shown also as means of attachment for the free ends of the strap parts.

Figure 5:
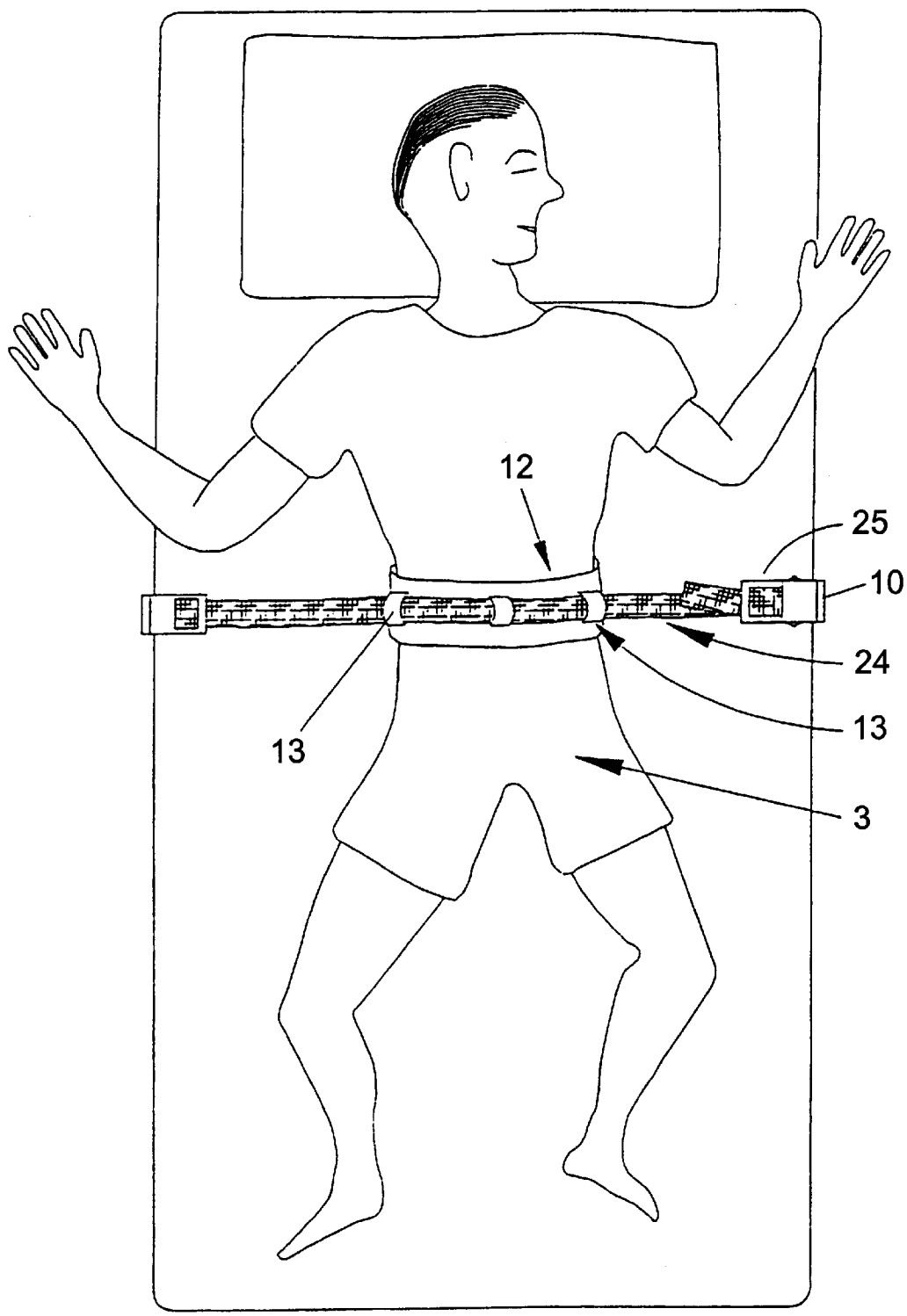
FIG. 5 is a plan view showing a second embodiment of the invention.

A second embodiment of the invention is shown in FIG. 5. In this embodiment a whole dress 3 is put on the person and a belt 12 is sewn up on the this dress. The strap 24 is fastened to the belt 12 by passing through at least two eyes 13, one on each side of the belt 12. The strap is fastened to the sides of the bed by attachments 10 as described above. A buckle 25 is arranged for straightening the strap.

The embodiments of the invention described above includes an article of dress 3. However, this part of the device can alternatively be a harness or the like. It is important that the harness is so formed that it can not rotate around the body of the person.

What is claimed is:

1. Device for preventing a person being in bed from turning his body in one or the other direction from a position lying on the stomach to a position lying on the back, said device including a harness, placed on or fastened around at least one part of the body, whereat two parts of a strap of about the same length extend from the backside of the harness and outwards adapted to be fastened to the two sides of the bed, each of the two strap parts having an inner end and an outer end with said inner ends being attached to the harness on one side of said harness, said outer ends being adapted to be secured to opposite sides of the bed, a length of the two strap parts allowing a person wearing the harness to turn about 90° from a position on the stomach to prevent the harness from further turning.

2. Device according to claim 1, wherein the two strap parts are one continuous band.

3. Device according to claim 1, wherein the harness is put on the upper body.

4. Device according to claim 1, wherein the harness is put on the lower part of the body.

5. Device for preventing a person lying on a supporting structure from turning his body in one or the other direction from a position lying on the stomach to a position lying on the back, said device including a harness, placed on or fastened around at least one part of the body, whereat two parts of a strap of about the same length extend from the backside of the harness and outwards adapted to be fastened to the two sides of the supporting structure, each of the two strap parts having an inner end and an outer end with said inner ends being attached to the harness on one side of said harness, said outer ends being adapted to be secured to opposite sides of the supporting structure, a length of the two strap parts allowing a person wearing the harness to turn about 90° from a position on the stomach to prevent the harness from further turning.

6. Device according to claim 5, wherein the two strap parts are one continuous band.

7. Device according to claim 5, wherein the harness is put on the upper body.

8. Device according to claim 5, wherein the harness is put on the lower part of the body.

9. A system for preventing a person lying on a supporting structure from turning his body in one or the other direction from a position lying on the stomach to a position lying on the back, said system including a harness, placed on or fastened around at least one part of the body to move with the movement of the body, whereat two parts of a strap of about the same length extend from the backside of the harness and outwards to the two sides of the supporting structure to be fastened there, each of the two strap parts having an inner end and an outer end with said inner ends being attached to the harness on one side of said harness, said outer ends being adapted to be secured to opposite sides of the supporting structure, a length of the two strap parts allowing a person wearing the harness to turn about 90° from a position on the stomach to prevent the harness from further turning.

10. The system according to claim 9, wherein the two strap parts are one continuous band.

11. The system according to claim 9, wherein the harness is put on the upper body.

12. The system according to claim 9, wherein the harness dress is put on the lower part of the body.

* * * * *